United States Patent [19]

Beeley et al.

[11] 4,450,170

[45] May 22, 1984

[54] TREATMENT OF DIARRHOEA WITH 2-AMINOIMIDAZOLINE DERIVATIVES

[75] Inventors: Lee J. Beeley, Dorking; Peter M. Newsome, Worcester Park, both of England

[73] Assignee: Beecham Group Limited, England

[21] Appl. No.: 277,034

[22] Filed: Jun. 24, 1981

[30] Foreign Application Priority Data

Jul. 9, 1980 [GB] United Kingdom ............... 8022407
Feb. 20, 1981 [GB] United Kingdom ............... 8105339

[51] Int. Cl.$^3$ ........................................... A61K 31/415
[52] U.S. Cl. ................................ 424/273 R; 548/315; 548/351
[58] Field of Search ................................. 424/273 R

[56] References Cited

U.S. PATENT DOCUMENTS

| | | | |
|---|---|---|---|
| 3,190,802 | 6/1965 | Zeile et al. ................ | 548/315 X |
| 4,265,900 | 5/1981 | Rasmussen et al. ........ | 548/315 X |
| 4,312,879 | 1/1982 | Lal ............................ | 424/273 R |
| 4,332,814 | 6/1982 | Newsome et al. .......... | 424/273 R |

FOREIGN PATENT DOCUMENTS

| | | | |
|---|---|---|---|
| 1929950 | 3/1970 | Fed. Rep. of Germany ...... | 548/315 |
| 1670274 | 7/1970 | Fed. Rep. of Germany ...... | 548/315 |
| 2806811 | 8/1979 | Fed. Rep. of Germany ...... | 548/315 |
| 2014575 | 8/1979 | United Kingdom ............... | 548/315 |

OTHER PUBLICATIONS

*Chemical Abstracts,* 94:132312d (1981) [Lal et al., *J. Clin. Pharmacol.* 1981, 21(1), 16–19].

*Primary Examiner*—Richard A. Schwartz
*Attorney, Agent, or Firm*—Jacobs & Jacobs

[57] ABSTRACT

Compounds A - B - C wherein A is 2 imidazolinyl or N-alkyl derivative thereof, B is oxygen, sulphur, $CR^1R^2$ wherein $R^1$ and $R^2$ are hydrogen or alkyl, or $NR^3$ wherein $R^3$ is hydrogen or alkyl, and C is a 5 - or 6 - membered carbo- or heterocyclic group having a nitrogen containing substituent and up to two other substituents, are useful in treatment of diarrhoea or scours. Certain compounds A - B - C are novel.

7 Claims, No Drawings

TREATMENT OF DIARRHOEA WITH 2-AMINOIMIDAZOLINE DERIVATIVES

This invention relates to the treatment of diarrhoea in animals including man, to formulations for use in such treatment, to a class of novel compounds having activity useful in such treatment and to processes for their production.

Diarrhoea (also referred to as scours in cattle, sheep and pigs) can be a severe disease particularly in young animals and can often result in death. Diarrhoea is also common amongst human travellers and those exposed to low standards of hygiene. The diarrhoea frequently involves colonisation of the small intestine with enteropathogenic strains of E. coli which produce heat stable and/or heat labile enterotoxins. Related enterotoxins are produced by other enteropathogens, for example, cholera, and also cause diarrhoea. These enterotoxins stimulate fluid secretion in the gut lumen and hence cause diarrhoea. The associated fluid loss may lead to loss of condition, reduced weight gain of livestock and often to death.

It has now been discovered that a certain class of compounds have activity useful in treating diarrhoea. In particular, these compounds inhibit small-intestinal secretion whilst having less CNS activity than α-agonists of similar structure.

Accordingly, the present invention provides a method for treating diarrhoea in animals including man, which method comprises administering an effective, non-toxic amount of a compound of formula (I):

$$A\text{—}B\text{—}C \qquad (I)$$

wherein
A is a 2-imidazolinyl group optionally substituted on a
nitrogen atom with $C_{1-4}$ alkyl group;
B is an oxygen or sulphur atom; $CR^1R^2$, wherein $R^1$ and $R^2$ are the same or different and each is selected from $C_{1-4}$ alkyl and hydrogen; or $NR^3$, wherein $R^3$ is selected from $C_{1-4}$ alkyl and hydrogen; and
C is a 5 or 6 membered carbo- or heterocyclic group having a nitrogen-containing substituent and optionally also substituted by one or two groups, each selected from halogen, $(C_{1-4})$ alkyl, $(C_{1-4})$ alkoxy and hydroxy; or an N-acyl derivative and/or an acid addition salt thereof, to an animal, including man, suffering from diarrhoea.

It will be appreciated that certain of the compounds of formula (I) may exist in distinct tautomeric forms. All such forms are useful in, and encompassed by, the present invention.

Any one or more of the available nitrogen atoms of a compound of formula (I) may be acylated. It will be appreciated that not all the nitrogen atoms may be available for acylation, thus when B is, for instance, a group $NR^3$ and $R^3$ is an alkyl moiety, only one of the nitrogen atoms of the imidazoline moiety may be acylated. However, if B is a group $NR^3$ and $R^3$ is hydrogen, both nitrogens of the imidazolinyl moiety may be acylated, or one of these nitrogens and the nitrogen atom of B may be acylated.

Suitable nitrogen containing substituents include groups of formula:

$$\text{—X—R}^4$$

wherein
X is methylene or a bond; and
$R^4$ is amino, mono- or di($C_{1-4}$) alkyl amino, amidino, guanidinyl or 2-imidazolinyl optionally substituted on a nitrogen atom with a ($C_{1-4}$) alkyl group.

Suitably A is 2-imidazolinyl or an acyl derivative thereof.

Suitably B is NH.

Suitably C is a substituted phenyl group having a nitrogen-containing substituent in the ortho or para position with respect to B.

Suitable acyl moieties are $C_{1-3}$ alkyl carbonyl, trihaloacetyl, benzoyl and phenacetyl groups.

Suitable salts are mono- and di-hydrochlorides, -hydrobromides, -hydroiodides, nitrates, sulphates, citrates, tartrates and pamoates.

Preferably the nitrogen containing substituent on C is amino, guanidinyl or aminomethyl.

When C is a substituted phenyl group it is preferred that there is a substituent in the position ortho to the group B. It is also preferred that the nitrogen-containing substituent is located in the para-position.

Preferred compounds within formula (I) include compounds of formula (II) as hereinafter defined and p-amino clonidine and salts thereof.

It will be appreciated that the effective dose of the compounds of the formula (I) will depend in the usual way upon factors such as the severity of the diarrhoea, the weight of the sufferer, the particular drug chosen, and on similar variables. However, as a guide, we believe that a suitable dose will be within the range 1 μg to 1 mg/kg a day as a single or divided dose.

Antibacterial agents such as penicillins, aminoglycosides and sulphonamides may also be administered as part of the treatment of diarrhoea in conjunction with the present method of treatment.

It is believed that this method of treatment may usefully be combined with oral rehydration therapy such as described in U.S. Pat. No. 4,164,568 or Belgian Pat. No. 872,647.

Compounds of formula (I) may be produced by known methods such as those described below in relation to compounds of formula (II) and used, for instance, for producing p-amino clonidine.

p-amino Clonidine can be prepared by known methods, such as that described in U.K. Pat. No. 1,450,250 wherein 2,6-dichloro-4-nitro aniline is treated with N-acetyl-2-imidazolidone, the acetyl moiety is removed and then the nitro group is reduced to an amino group, for instance, by the method of Rouot and Leclerc, *Bull. Soc. Chem. Fr.*, (1979), 520. Other methods for producing p-amino clonidine will be apparent to those skilled in the art, however, it should be noted that these will usually involve the use of a 2,6-dichloro aniline derivative bearing in the 4-position a protected amino group, or a precursor for an amino group, such as the nitro group mentioned above, and the step of converting such a 4-substituent to an amino group.

Salts of p-amino clonidine can be prepared by known methods. The preparation of both the hydrochloride and dihydrochloride is disclosed by Rouot and Leclerc (above).

Certain compounds of formula (I) are novel:

Accordingly, the present invention provides compounds of formula (II)

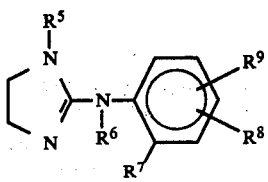

wherein
R⁵ is hydrogen, ($C_{1-4}$) alkyl or acyl;
R⁶ is hydrogen, ($C_{1-4}$) alkyl or acyl;
R⁷ is hydroxy, halogen, ($C_{1-4}$) alkyl, ($C_{1-4}$) alkoxy or a group R⁸;
R⁸ is an ortho or para substituent selected from amino, mono- or di-($C_{1-4}$) alkyl amino, aminomethyl, mono- or di-($C_{1-4}$) alkylaminomethyl, amidino, guanidinyl or 2-imidazolidinyl optionally substituted on a nitrogen atom with ($C_{1-4}$) alkyl or acyl;
R⁹ is selected from hydroxy, halogen, ($C_{1-4}$) alkoxy, hydrogen and a group R⁸ when in the para position or R⁹ is selected from hydroxy, halogen, ($C_{1-4}$) alkyl, and ($C_{1-4}$) alkoxy when in a meta position,
or R⁹ is selected from hydroxy, halogen, ($C_{1-4}$) alkyl, ($C_{1-4}$) alkoxy and a group R⁸ when in the ortho position,
or a salt thereof, provided that when R⁹ is in the ortho position and is chloro, R⁷ is chloro, R⁵ is hydrogen and R⁶ is hydrogen, ethyl or acetyl, then R⁸ is other than para-amino, or a methyl, ethyl or acetyl derivative or salt thereof.

Preferably R⁵ and R⁶ are hydrogen.
Preferably R⁸ is at the 4-position.
Preferably R⁷ and R⁹ are the same and are at the 2,6 positions.
Preferably R⁸ is amino, substituted amino or guanidinyl.
Preferred compounds within formula (II) include:
2,6-dimethyl-4-aminophenylamino-2-imidazoline;
2,6-dibromo-4-aminophenylamino-2-imidazoline.

It will be appreciated that certain compounds of formula (II) will exist in tautomeric forms of the structure shown above. The present invention embraces all such tautomers.

Salts of compounds of formula (II) need not be pharmaceutically acceptable; if they are not they may be useful in purification of compounds of formula (II).

The present invention also provides compounds of formula (II) for use in treating diarrhoea.

According to the present invention there is also provided a process for producing a compound of formula (II) which process comprises
(a) reacting a compound of formula (IV)

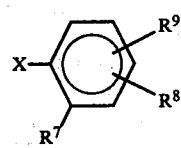

wherein
R⁷ to R⁹ are as defined with respect to formula (II)
and
X is a group

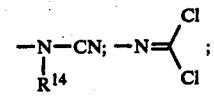

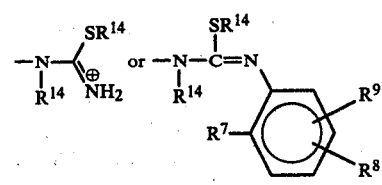

wherein
R¹⁴ is an ($C_{1-4}$) alkyl group, with a compound of formula (III)

$$H_2N-CH_2-CH_2-NHR^{19}$$ (III)

wherein R¹⁹ is hydrogen or ($C_{1-4}$) alkyl.
(b) reacting a compound of formula (V)

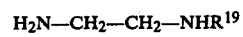

wherein
R⁷-R⁹ are as defined with respect to formula (II),
and
R¹⁵ is hydrogen or a group R⁶ as hereinbefore defined with respect to formula (II), with a compound of formula (VI)

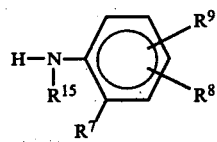

wherein
R²⁰ is hydrogen, alkyl or, when R¹⁷ and R¹⁸ are oxo, acyl,
R¹⁶ and R¹⁷ together form a bond and R¹⁷ is ($C_{1-4}$) alkylthio or benzylthio
or R¹⁶ is hydrogen,
and R¹⁷ and R¹⁸ together form an oxo group;
or (c) converting the corresponding compound with a nitro substituent in the ortho or para position to the required compound of formula (II);
and optionally thereafter forming an acyl derivative and/or a salt thereof.

Process (a) may be conducted according to the process described in UK Pat. No. 1,229,995 when X is

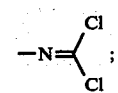

according to the process described in Netherlands Pat. No. 6,411,516 (*Chem. Abs.* 63, P18102 g) when X is

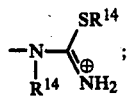

according to the process described in *Chem. Abs.*, 85, P94364b when X is

and according to the process described in *Chem. Abs.*, 85, P5633g when X is

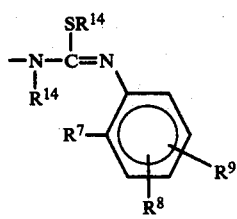

Process (b) may be conducted according to the process described in German Offenlegungschrift No. 2,505,297 or Netherlands Pat. No. 7,404,472 when $R^{17}$ and $R^{18}$ together form an oxo group, and according to the process described in *Chem. Abs.*, 84, P59465t when $R^{16}$ and $R^{17}$ together form a bond.

Process (c) may be conducted according to the process described in Rouot & Leclerc (supra) or in European Patent Application No. 12,822, German Offenlegungsschrift No. 2,806,811 and U.K. Pat. No. 1,180,766.

The starting materials may be produced by conventional methods, as may the salts and acyl derivatives of compounds of formula (II).

The present invention further provides a pharmaceutical composition comprising a compound of formula (I) and a pharmaceutically acceptable carrier therefor.

As used herein the term 'pharmaceutical composition' includes compositions suitable for human and/or animal use and 'pharmaceutically acceptable' includes veterinarily acceptable.

Pharmaceutical compositions of compounds of formula (I) will, of course, be adapted for administration to humans or the animals to be treated.

Thus for example the composition may be a shaped composition, such as a bolus, tablet or capsule. In such cases the pharmaceutically acceptable carrier will be chosen from the usual range of lubricants, dispersants, binders, fillers and the like. When these shaped compositions are for administration to cattle and pigs, often they will weight at least 1 g, on occasions at least 2 g.

For administration to humans, especially young ones, the drug may suitably be presented as a syrup including suitable colouring and/or flavouring agents. Such syrups are conveniently presented in unit or multi-dose containers.

For veterinary use the composition may also be a dispersion or a solution of a compound of formula (I) (hereinafter referred to as 'the drug') in a suitable vehicle for use with an oral doser (this is a well known item of farm equipment, basically comprising a liquid reservoir, a mouthpiece adapted for insertion into animal mouths, and a pump mechanism whereby unit doses can be ejected from the reservoir through the mouthpiece). Conveniently the vehicle will be an oil or water based cream to ensure homogeneity of the unit doses administered. Alternatively, the drug may be administered as an aqueous solution using an oral doser.

The invention, therefore, also provides an oral doser containing a multi-dose of the drug in a veterinarily acceptable vehicle.

The drugs of the invention may also be added to the animal feed or drinking water. Thus the invention also provides animal feed or animal drinking water containing a compound of formula (I). It will be convenient to formulate these animal feed and drinking water compositions with a multi-dose of the drug so that the animal takes in an appropriate quantity of the drug along with its diet. It will also be convenient to present the composition of the invention as pre-mixes for addition to the feed or drinking water.

With young humans or animals, a particularly useful technique is to blend their milk with the drugs of this invention.

The compositions of the invention may also be formulated for injection. In such cases the drug chosen is suitably dissolved in water for injection.

Often it will be appropriate to include in the compositions a further medicine such as an antibacterial agent, for example an antibiotic such as amoxycillin or neomycin or a sulphonamide such as sulfadoxin.

Clearly the compositions of the invention will contain sufficient drug to enable this effective dose to be administered in convenient manner. Thus by way of example useful dosage units of the composition may contain 1 $\mu$g to 50 mg of the drug, more suitably 20 $\mu$g to 20 mg. Of course, it will be appreciated that many preferred compositions of the invention are in multi-dose form, as for the therapy of animals, it is often most desirable to be able rapidly to treat a number of animals. Such multi-dose compositions will contain by way of example, at least 1 mg of the drug. Depending on the exact nature of the said multi-dose composition, often it will contain at least 50 mg of the drug, and on occasions as much as 1 g.

Biological Evaluation of p-amino Clonidine dihydrochloride

The following tests were carried out:

1. Mice

Infant mice are separated from their mothers shortly before use. Animals up to 15 days of age are suitable for use but normally animals 7-9 days of age are used. Groups of animals are dosed with the compound 45 mins prior to oral challenge with 0.05-0.10 ml of culture filtrate prepared from an enteropathogenic strain of *E. coli*. Control animals receive drug vehicle 45 mins prior to challenge with a similar amount of culture filtrate. The compounds are administered orally. Animals are killed two hours later and the entire intestine removed. The ratio of gut weight to remaining bodyweight (GW/BW) is determined from each animal and the increase in this ratio is determined by subtracting 0.06 (GW/BW for untreated mice) from the GW/BW of the animal. Drug treated animals are compared with untreated controls. If the compound has had an effect in inhibiting the fluid secretion caused by the enterotoxin(s) present in the culture filtrate then the gut weight/bodyweight ratio should be reduced in the treated animals. The percentage fluid inhibition is determined from the formula:

$$100 - \left[ \frac{\text{Mean increase in } GW/BW \text{ ratio in treated animals}}{\text{Mean increase in } GW/BW \text{ ratio in control animals}} \times 100 \right]$$

Results are given in the table below, as are comparative results for the known anti-diarrhoeal, Loperamide.

p-Amino clonidine dihydrochloride

| Dose (mg/kg) | % fluid inhibition |
|---|---|
| 50 | 78 |
| 10 | 59 |
| 1 | 53 |
| 0.1 | 48 |
| 0.01 | 36 |
| 0.001 | 29 |

The calculated $ED_{50}$ of p-amino Clonidine dihydrochloride in the mouse is 0.25 mg/kg.

Loperamide

| Dose (mg/kg) | % fluid inhibition |
|---|---|
| 4 | 45 |
| 1 | 18 |

These results clearly demonstrate the high level of activity of the p-amino Clonidine dihydrochloride in the reduction of fluid secretion caused by challenge with an enteropathogenic strain of *E. coli.*

The activity of the p-amino Clonidine dihydrochloride is highlighted by comparison with Loperamide, which as can be seen from the Table, is considerably less active than the p-amino Clonidine dihydrochloride in the mouse test.

2. Calf Thiry-Vella Intestinal Loop Model

In vivo tests were conducted using male castrate calves, each with two surgically prepared Thiry-Vella intestinal loops prepared as described by R. J. Bywater, *J. Comp. Path.,* 80, 565, (1970).

The loops are washed with saline and then a saline bolus is left in the loops for 30 minutes to establish a basal absorptive rate. After 30 minutes the fluid in the loops is removed and measured. Heat stable *E. coli* enterotoxin from *E. coli* strain p16 is added to the loop infusate which is then returned to the loops.

After a further 30 minutes the content of the loops is measured once more and at this time drug is added to the test loop perfusate.

Measurements of absorption or secretion from the loops are made every 30 minutes over the subsequent 2½ hours.

The results are expressed in terms of fluid (ml) secreted into or absorbed from the loops after each 30 minute period. A minimum of six observations are undertaken with each experimental compound. Perfusion periods in which drugs are present in a loop are alternated with perfusion periods in which drug is absent from the same loop.

Calf-Thiry Vella Intestinal Loop Model

| Time (min) (after toxin administration) | *Secretion (ml/30 min) | |
|---|---|---|
| | Control | 1 µg/kg p-Amino Clonidine≠ |
| −30−0 | −3 | −3 |
| 0−30+ | 27 | 25 |
| 30−60 | 19 | 6** |
| 60−90 | 12 | 2** |
| 90−120 | 11 | 0** |
| 120−150 | 11 | −1** |
| 150−180 | 11 | −1** |

*A negative value denotes absorption of fluid
**Denotes significantly different fluid secretion from control (P < 0.05 students t test)
+ Drug administered 30 min. after toxin
≠ Administered as the dihydrochloride Toxicity The drugs have been found to have a satisfactory therapeutic ratio.

3. Piglets (a) Inhibition of Diarrhoea Induced by Enterotoxin Administration

2–4 day old piglets were dosed with the compound orally 45 mins prior to oral challenge with 25 ml of culture filtrate prepared from an enteropathogenic strain of *E. coli.* Control animals received drug vehicle 45 mins prior to challenge with a similar volume of material. Animals were observed for diarrhoea over a 6 hour period and the severity of scour scored on a 0-3 basis for each animal at hourly intervals. After 6 hours observation some piglets were given a second dose of drug (or placebo) and observations were continued for a further six hours. The percentage inhibition in treated animals was determined as:

$$100 - \left[ \frac{\text{Mean score of scour in treated animals}}{\text{Mean score of scour in control animals}} \times 100 \right]$$

(b) Inhibition of Diarrhoea Resulting from *E. coli* Infection

Colostrum deprived piglets were infected with 5 ml of an overnight culture containing $10^8$-$10^9$ viable *E. coli* P16/ml. The following day, piglets were matched by weight and scour score and then treated and observed for 6 hours in a similar manner to toxin challenged piglets, as described above.

RESULTS (a) Effect of Compounds of Piglet Diarrhoea Induced by Enterotoxin Administration (Groups of 6 piglets)

| Compound | Dose | Duration of test | Mean Scour Score ± SEM | | % inhibition of scour | Significance |
|---|---|---|---|---|---|---|
| | | | Placebo treated | Drug treated | | |
| 2-(4-amino-2,6-dimethyl/phenyl-amino)imidazoline dihydrochloride | 200 µg/Kg po | 6 hr | 2.2 ± 0.1 | 0.5 ± 0.2 | 78% | P < 0.001 |
| | 100 µg/Kg po | 6 hr | 2.0 ± 0.3 | 0.6 ± 0.3 | 69% | P < 0.05 |
| | 100 µg/Kg po × 2 | 12 hr | 1.5 ± 0.3 | 0.6 ± 0.2 | 62% | P < 0.05 |

-continued

| Compound | Dose | Duration of test | Mean Scour Score ± SEM | | % inhibition of scour | Signif- cance |
|---|---|---|---|---|---|---|
| | | | Placebo treated | Drug treated | | |
| p-amino Clonidine dihydrochloride | 100 μg/Kg po | 6 hr | 2.0 ± 0.5 | 0.4 ± 0.2 | 79% | $P < 0.01$ |

(b) Effect of p-amino Clonidine dihydrochloride on Piglet Diarrhoea induced by infection with E. coli P16
(Groups of 8 piglets)

| Group | Treatment | Mean Scour Score ± SEM | % Inhibition of scour | Mortality over 7 days |
|---|---|---|---|---|
| A | Placebo | 2.9 ± 0.1 | 0% | 25% |
| B | Neomycin 30 mg/Kg po | 2.4 ± 0.2 | 16% | 0% |
| C | Neomycin 30 mg/Kg po + p-amino Clonidine dihydrochloride 100 μg/Kg po | 1.3 ± 0.4 | 54% | 0% |

A significant difference in scour was noted between groups A and C ($P<0.01$) and between groups B and C ($P<0.01$). The difference between groups A and B was not significant (Analysis of variance).

FORMULATIONS OF THE DRUGS

Example 1 p-Amino Clonidine bolus 0.2 mg
Boluses of the following composition were prepared:

| | |
|---|---|
| p-Amino Clonidine dihydrochloride | 0.2 mg |
| Microcrystalline cellulose | 500 mg |
| Corn starch | 250 mg |
| Magnesium stearate | 25 mg |
| Lactose, anhydrous | to 2500 mg |

The ingredients were passed through a 30 mesh stainless steel screen and blended in a suitable blender. The resultant compression mix was compressed directly on a tabletting machine to give tablets each containing 0.2 mg p-amino Clonidine dihydrochloride.

Example 2 p-Amino Clonidine Oral Doser 0.1 mg
1 Kg of the following composition was prepared:

| | % by wt. |
|---|---|
| p-Amino Clonidine dihydrochloride | 0.01 |
| Aluminium stearate | 6.0 |
| Sunflower oil | to 100 |

The aluminium stearate was dispersed with stirring in a portion of the sunflower oil heated to 115° C. The dispersion was added to the rest of the sunflower oil heated to 140° C. The gel was stirred at 130° C. for 15 minutes and then allowed to cool without stirring to room temperature. The milled p-Amino Clonidine dihydrochloride was dispersed in the cooled gel base and then passed through a colloid mill to produce a fine, homogenous dispersion. The dispersion was filled into plastic bottles fitted with a dosing pump.

Example 3 p-Amino Clonidine Injection 0.25 mg/ml
1 Liter of the following composition was prepared:

| | % w/v |
|---|---|
| p-Amino Clonidine dihydrochloride | 0.025 |
| Sodium chloride | 0.5 |
| Water for injections | to 100 |

The p-amino Clonidine dihydrochloride and sodium chloride were dissolved in the water for injections and the solution was filtered and filled into glass ampoules. The ampoules were sterilised by autoclaving.

Example 4 p-Amino Clonidine Premix
A premix of the following composition was prepared:

| | % by wt. |
|---|---|
| p-Amino Clonidine dihydrochloride | 1.0 |
| Limestone flour | to 100 |

The ingredients were mixed together in a ribbon blender to give a homogenous mixture. The premix was mixed into animal feed at the rate of 1 kg per metric ton to provide a concentration of 10 g of p-amino Clonidine dihydrochloride per metric ton.

Example 5 p-Amino Clonidine Soluble Powder
1 Kg of the following composition was prepared:

| | % by wt. |
|---|---|
| p-Amino Clonidine dihydrochloride | 0.1 |
| Lactose | to 100 |

The p-Amino Clonidine dihydrochloride and lactose were sieved and mixed together in a suitable blender to give a homogenous powder. The powder was filled into jars. The powder was used at the rate 0.5 g per gallon of drinking water to medicate pigs.

Example 6

Oral Rehydration Formulation containing p-amino Clonidine 1 kg of the following composition was prepared by mixing together the ingredients in dry powder form:

| | | |
|---|---|---|
| Glycine | 10.3% | |
| Dextrose (anhydrous) | 67.6 | |
| Sodium Chloride | 14.3 | |
| Potassium Dihydrogen Phosphate | 6.8 | |
| Citric Acid | 0.8 | |
| Tri-potassium Citrate | 0.2 | |
| p-amino Clonidine dihydrochloride | 0.002 | |

60 g of the composition was then dissolved in 2 liters of water and fed to diarrhoeic calves.

Example 7

In the formulation of Example 6 p-amino Clonidine dihydrochloride was replaced by 2-(4-amino-2,6-dimethylphenylamino)-imidazoline dihydrochloride.

Example 8

The following formulation may be prepared by the method set out below:

| | |
|---|---|
| p-amino Clonidine dihydrochloride | 0.01% w/v |
| Bentone 38 (1) | 1.5% w/v (i.e. 1.5 g/100 ml) |
| Propylene Carbonate | 0.6% w/v |
| Pharmasorb (2) | 10% w/v |
| Phosphoric Acid (3) | 0.1% w/v |
| Ampicillin Trihydrate | 6.0% w/v as free acid |
| Soya-Bean Oil | to 100% |

(1) Bentone 38 is dimethyl dioctadecyl 125 hectorite, [Mg$_8$LiSi$_{12}$O$_{30}$(OH)$_6$]$^\ominus$[(CH$_3$)$_2$N(C$_{18}$H$_{37}$)$_2$]$^\ominus$
(2) Pharmasorb is a brand of activated Attapulgite.
(3) The phosphoric acid is present in the minor proportion to balance the alkaline pH of the Bentone.

The Bentone was dispersed in the soya-bean oil, and when thoroughly distributed, the propylene carbonate was added with high speed mixing, followed by colloid milling to produce the base. Into this base was first mixed the phosphoric acid, and then the pharmasorb and the penicillin, and the resultant suspension was then passed through a colloid mill once more.

Example 9

Example 8 was repeated, but using amoxycillin trihydrate in place of the ampicillin trihydrate.

Example 10

The following formulation was prepared by the method of Example 8:

| | |
|---|---|
| p-amino Clonidine dihydrochloride | 0.01% w/v |
| Sunflower Oil | 1.75% w/v |
| Propylene Carbonate | 0.6% w/v |
| Pharmasorb | 10.0% w/v |
| Ampicillin Trihydrate | 5.0% w/v |
| Sunflower Oil | to 100% |

(1) Bentone 27 is dimethyl benzyl octadecyl ammonium hectoriete, [Mg$_8$LiSi$_{12}$O$_{30}$(OH)$_6$]$^\ominus$[(CH$_3$)$_2$N(C$_{18}$H$_{37}$)(CH$_2$C$_6$H$_5$)]$^\oplus$

Example 11

Example 10 was repeated, but using amoxycillin trihydrate in place of the ampicillin trihydrate.

Example 12

2-(4-amino-2,6-dibromophenylimino)imidazolidine

A solution of concentrated hydrochloric acid (2.8 ml, 0.028 M) in aqueous ethanol (50%, 15 ml) was added dropwise to a stirred heated mixture of 2-(2,6-dibromo-4-nitro phenylimino)imidazolidine (4 g, 0.011 M) and iron powder (1.9 g, 0.034 M) in aqueous ethanol (50%). The mixture was heated under reflux for 3 hours after which time it was filtered hot and evaporated to a low volume. This residual solution was acidified with dilute hydrochloric acid and the resulting solid was removed. The solution was then basified with dilute aqueous sodium hydroxide yielding a solid which was collected. This solid was triturated with hot methanol which was then evaporated to leave a brown solid (3.2 g). This solid was chromatographed on alumina and eluted with a methanol in methylene chloride gradient. The fractions containing the required compound were combined and evaporated affording 2-(4-amino-2,6-dibromophenylimino)imidazoline dihydrochloride, mp>320° C. (1.6 g).

Analysis calculated for $C_9H_{12}Br_2Cl_2N_4$; Theory: C 26.56; H 2.97; N 13.77; Found: C 27.07; H 3.02; N 13.79.

Example 13

2-(4-amino-2,6-dimethylphenylimino)imidazolidine

The 2-(2,6-dimethyl-4-nitrophenylimino)imidazolidine (8.75 g) was reduced with iron and hydrochloric acid in aqueous ethanol according to the process of Example 12. The product was chromatographed on a silica column and eluted with a methanol in methylene chloride gradient. The fractions containing the required compound were evaporated and the residue was treated with ethanolic hydrochloric acid to give 2-(4-amino-2,6-dimethylphenylimino)imidazolidine dihydrochloride. An analytical sample was recrystallised as the mono-hydro-iodide salt, mp 252°–253° C.

Example 14

2-(4-amino methyl-2,6-dichlorophenylimino)imidazolidine

Borane methyl sulphide complex (10.7 ml, 0.107 M) was added slowly to 2-(4-carboxamido-2,6-dichlorophenylimino) imidazolidine (8.0 g, 0.029 M) in dry tetrahydrofuran (160 ml) under nitrogen with stirring. The reaction mixture was heated under reflux for 3 hours and cooled to room temperature. Methanol was added until the mixture became clear and stirring was continued for 12 hours. Hydrogen chloride gas was bubbled into the mixture for 15 min and then the mixture was heated under reflux for 1 hour. It was then evaporated and the residue was taken up in water. The solution was basified with sodium hydroxide solution and the resulting oily solid was collected and crystallised from acetone. This solid was dissolved in dilute hydrochloric acid, filtered and basified with sodium hydroxide solution yielding the 2-(4-aminomethyl-2,6-dichlorophenylimino)imidazolidine. An analytical sample was recrystallised as the mono hydro-iodide salt, mp 205°–206.5° C.

Example 15

2-(2,6-dichloro-4-diethylaminomethyl-phenylimino)imidazolidine

Lithium aluminium hydride (3.4 g, 0.08 M) was added portionwise to 2-(4-diethylcarboxamido-2,6-dichlorophenyl imino)imidazolidine (3.4 g, 0.01 M) in ether (350 ml) with stirring. After 2.5 hours ethyl acetate was added followed by methanol. The mixture was then evaporated and dilute sodium hydroxide was added to the residue. The residue was extracted with methylene chloride and the extract was evaporated to give the required compound as an oil (3.3 g) which was recrystallised as 2-(2,6-dichloro-4-diethylaminomethyl-phenylimino)imidazolidine dihydrochloride, MP 272°–274° C.

Example 16

2-(2,6-dichloro-4-imidazolino-2-imino-phenylimino)imidazolidine

A mixture of 2-(4-amino-2,6-dichlorophenylimino) imidazolidine (3.7 g, 0.015 M) and 1-acetyl-2-imidazolidone (2.2 g, 0.02 M) in phosphoryl chloride (25 ml) was heated under reflux for 3 days. After cooling to room temperature the phosphoryl chloride was evaporated to give an oily residue. The residue was basified with sodium hydroxide (50%) and the insoluble solid was filtered off. This solid was hydrolysed with dilute sodium hydroxide in methanol. After evaporation of the mixture the product was extracted into methylene chloride. Evaporation of the extract gave a gum which crystallised giving 2-(2,6-dichloro-4-imidazolino-2-imino-phenylimino)imidazolidine dihydroiodide, MP 298°–300° C.

Example 17

2-[2,6-dichloro-4-(1,3-dimethylguanidino)-phenylimino]imidazolidine

Phosphoryl chloride (4.4 ml, 0.047 M) was added with cooling to dimethylurea (4 g, 0.045 M) in tetrahydrofuran (60 ml). After stirring at room temperature for 5 hours the mixture was added to 2-(4-amino-2,6-dichlorophenylimino) imidazolidine (3.0 g, 0.012 M) in tetrahydrofuran (60 ml). The mixture was refluxed for 18 hours and then evaporated to give an oily solid. The residue was extracted into 2 M HCl, washed with methylene chloride and then basified. Extraction of the alkaline mixture with methyl chloride yielded a gum on evaporation of the extract. The gum was taken up in ethanol and the required guanidino compound (300 mg) crystallised. The product was recrystallised as 2-[2,6-dichloro-4-(1,3-dimethylguanidino)-phenylimino]imidazolidine dihydroiodide (MP 320° C.).

Analysis calculated for $C_{12}H_{18}N_6Cl_2I_2$; Theory: C 25.24; H 3.18; N 14.72; Found: C 24.91; H 3.47; N 14.92.

Example 18

The activity of various compounds of formula (I) was assessed in mice by the method given above. The results were as follows:

| Compound of Example No. | $R_5$ | $R_6$ | $R_a$ | $R_b$ | $R_{11}$ | dose mg/Kg | % inhibition |
|---|---|---|---|---|---|---|---|
| — | H | $CH_3$ | p-$NH_2$ | o-Cl | Cl | 200 | 72 |
|   |   |   |   |   |   | 50 | 62 |
|   |   |   |   |   |   | 10 | 37 |
| — | H | H | p-NHEt | o-Cl | Cl | 200 | 97 |
|   |   |   |   |   |   | 50 | 79 |
|   |   |   |   |   |   | 10 | 59 |
| — | H | H | p-NHOAc | o-Cl | Cl | 200 | 57 |
|   |   |   |   |   |   | 50 | 48 |
|   |   |   |   |   |   | 10 | 42 |
| — | H | H | p-$NH_2$ | o-Cl | Cl | 50 | 78 |
|   |   |   |   |   |   | 10 | 59 |
| — | H | H | p-$NH_2$ | H | Cl |   |   |
| 15 | H | H | p-$CH_2NEt_2$ | o-Cl | Cl | 500 | 42 |
|   |   |   |   |   |   | 200 | 37 |
|   |   |   |   |   |   | 50 | 28 |
| 13 | H | H | p-$NH_2$ | o-Cl | $CH_3$ | 200 | 69 |
|   |   |   |   |   |   | 50 | 54 |
|   |   |   |   |   |   | 10 | 66 |
| 12 | H | H | p-$NH_2$ | o-Br | Br | 200 | 85 |
|   |   |   |   |   |   | 50 | 65 |
|   |   |   |   |   |   | 10 | 48 |
| 17 | H | H | p-N=C(NHMe)(NHMe) | o-Cl | Cl | 200 | 53 |
|   |   |   |   |   |   | 50 | 37 |
|   |   |   |   |   |   | 10 | 33 |
| 14 | H | H | p-$CH_2NH_2$ | o-Cl | Cl | 200 | 39 |
|   |   |   |   |   |   | 50 | 38 |
| 16 | H | H | p-N=(imidazolidine) | o-Cl | Cl | 400 | 41 |
|   |   |   |   |   |   | 100 | 29 |

We claim:

1. A pharmaceutical composition for the treatment of diarrhoea in animals including man, comprising an effective, non-toxic amount of p-amino clonidine or a pharmaceutically acceptable N-carboxylic acid acyl derivative thereof and/or a pharmaceutically acceptable acid addition salt thereof in combination with an oral rehydration formula.

2. A mehthod for treating diarrhoea in animals including man, which comprises administering an effective, non-toxic amount of p-amino clonidine or a pharmaceutically acceptable N-carboxylic acid acyl derivative and/or pharmaceutically acceptable acid addition salt thereof, to an animal, including man, suffering from diarrhoea.

3. The method according to claim 2, wherein p-amino clonidine or a pharmaceutically acceptable acid addition salt thereof is administered.

4. A method for treating diarrhoea in animals including man, which comprises administering an effective, non-toxic amount of a compound of formula (I):

$$A\text{—}B\text{—}C \tag{I}$$

wherein

A is 2-imidazolinyl optionally substituted on a nitrogen atom with $C_{1-4}$ alkyl;

B is $NR^3$, where $R^3$ is $C_{1-4}$ alkyl or hydrogen; and

C is phenyl being substituted by unsubstituted guanidino or guanidino substituted by one or more $C_{1-4}$ alkyl; said phenyl being optionally substituted by one or two groups, each selected from halogen, $(C_{1-4})$ alkyl, $(C_{1-4})$ alkoxy and hydroxy;

or a pharmaceutically acceptable N-carboxylic acid acyl derivative and/or pharmaceutically acceptable acid addition salt thereof, to an animal, including man, suffering from diarrhoea.

5. The method according to claim 4, wherein C is phenyl substituted by unsubstituted guanidino and optionally substituted by one or two groups, each selected from halogen, $(C_{1-4})$ alkyl, $(C_{1-4})$ alkoxy and hydroxy.

6. The method according to claim 4, wherein C is phenyl substituted by di$(C_{1-4})$ alkylguanidino and optionally substituted by one or two groups, each selected from halogen, $(C_{1-4})$ alkyl, $(C_{1-4})$ alkoxy and hydroxy.

7. A pharmaceutical composition for the treatment of diarrhoea in animals including man, comprising an effective, non-toxic amount of a compound as defined in claim 4 or a pharmaceutically acceptable N-carboxylic acid acyl derivative thereof and/or a pharmaceutically acceptable acid addition salt thereof in combination with an oral rehydration formulation.

* * * * *